US012805805B2

(12) United States Patent
Elyada et al.

(10) Patent No.: US 12,805,805 B2
(45) Date of Patent: Nov. 24, 2026

(54) BODY SHAPE COMPLIANT WEARABLE PHYSIOLOGICAL MONITOR AND SYSTEM

(71) Applicant: ATLASense Biomed, Ltd., Hod Hasharon (IL)

(72) Inventors: Ori Elyada, Bnei Zion (IL); Hagai Shvadron, Beit Alfa (IL); Tal Or, Hod Hasharon (IL); Shimon Yisraelian, Nes Ziona (IL)

(73) Assignee: ATLASense Biomed, Ltd., Hod Hasharon (IL)

( * ) Notice: Subject to any disclaimer, the term of this patent is extended or adjusted under 35 U.S.C. 154(b) by 203 days.

(21) Appl. No.: 18/632,849

(22) Filed: Apr. 11, 2024

(65) Prior Publication Data

US 2024/0341684 A1 Oct. 17, 2024

Related U.S. Application Data

(60) Provisional application No. 63/495,781, filed on Apr. 13, 2023.

(51) Int. Cl.

*A61B 5/00* (2006.01)
*A61B 5/11* (2006.01)
*A61B 5/257* (2021.01)

(52) U.S. Cl.

CPC .......... *A61B 5/6831* (2013.01); *A61B 5/0002* (2013.01); *A61B 5/11* (2013.01); *A61B 5/257* (2021.01); *A61B 5/6833* (2013.01); *A61B 5/742* (2013.01); *A61B 2560/0219* (2013.01); *A61B 2560/0456* (2013.01); *A61B 2562/227* (2013.01)

(58) Field of Classification Search

CPC .... A61B 2560/0219; A61B 2560/0456; A61B 2562/227; A61B 5/0002; A61B 5/11; A61B 5/1116; A61B 5/257; A61B 5/6831; A61B 5/6833; A61B 5/742

See application file for complete search history.

(56) References Cited

U.S. PATENT DOCUMENTS

| | | | | |
|---|---|---|---|---|
| 11,058,314 B1 * | 7/2021 | Galgalikar | ........... | A61B 5/0006 |
| 11,589,792 B1 | 2/2023 | Abercrombie, II et al. | | |
| 2015/0022372 A1 * | 1/2015 | Vosch | .................. | A61B 5/0006 340/870.07 |

(Continued)

FOREIGN PATENT DOCUMENTS

| | | |
|---|---|---|
| WO | 2020095296 A1 | 5/2020 |
| WO | 2023043866 A1 | 3/2023 |

*Primary Examiner* — Amanda K Hulbert
(74) *Attorney, Agent, or Firm* — Polsinelli PC

(57) ABSTRACT

A wearable physiological monitor (WPM) and system, compliant in shape to a subject's body, that collects physiological parameter information from a subject's body and conveys it to a receiver. In one embodiment, central housing includes a direct skin contacting (DSC) sensor in direct contact with the subject's body, that collects the parameter information and conveys to other parts of the central housing. In one embodiment, a system includes a WPM and a strap, wherein the strap includes a hole through which a DSC sensor may be located, and includes also additional embedded sensors. In one embodiment, a charging base for a WPM has tapered walls and a connection to a power source that permit easy and accurate placement in the base by a combination of gravity and magnetic forces.

13 Claims, 9 Drawing Sheets

(56) References Cited

U.S. PATENT DOCUMENTS

| | | | | |
|---|---|---|---|---|
| 2015/0082623 | A1* | 3/2015 | Felix | A61B 5/273 29/825 |
| 2016/0262649 | A1* | 9/2016 | Hayes-Gill | A61B 5/288 |
| 2016/0317057 | A1* | 11/2016 | Li | A61B 5/6833 |
| 2017/0095177 | A1* | 4/2017 | Spencer | A61B 5/0006 |
| 2019/0150739 | A1 | 5/2019 | Wawro et al. | |
| 2021/0169369 | A1 | 6/2021 | Shurtliff et al. | |
| 2022/0039720 | A1* | 2/2022 | Abercrombie, II | A61B 5/02438 |
| 2022/0296165 | A1 | 9/2022 | Datta et al. | |

* cited by examiner

BODY SHAPE COMPLIANT WEARABLE PHYSIOLOGICAL MONITOR AND SYSTEM

CROSS-REFERENCE TO RELATED APPLICATION(S)

This application claims priority from provisional U.S. Pat. App. No. 63/495,781, filed on Apr. 13, 2023, which is hereby incorporated by reference in its entirety.

BACKGROUND

Wearable physiological monitors (WPM) are attached to the body of a subject. WPMs may be intended for medical use or for non-medical use such as wellness or sports. This patent concerns a subset of WPM that attach to a subject including, but not limited to, using skin-adhesive means such as "ECG electrodes" or "patches" described hereinbelow and/or using an external restraining means such as a strap, belt or article of clothing. This patent generally excludes wrist-worn WPMs "watches", "wrist bands" and also excludes mobile physiological monitors that are not mechanically attached to the subject's body such as some models of Holter recorders and cardiac telemetry transmitters that are carried by the subject but only connected to the subject's body by means of loose lead wires. This patent mostly addresses WPMs that are worn on the upper-chest, lower-chest, abdomen, waist and/or back, but is also applicable to other body areas such as, but not limited to, upper arms, thighs, buttocks, neck or any other body area.

WPMs include a variety of sensors, some are electrophysiological (EP) and require electrical body contacts called "Electrodes".

Electrodes can be used for sensing a variety of physiological signals including, for example, ElectroCardiogram (ECG aka EKG), ElectroMyograph (EMG), Skin Conductance Level (SCL aka GSR), and Bio Impedance (BioZ). Electrodes may also be used for auxiliary functions such as providing a DC voltage bias to the body.

Electrodes can be of several types (1) "wet electrodes" comprise of a conductive sponge or hydrogel embedded within an adhesive sticker that provides a mechanical connection to the skin, most off-the-shelf "ECG electrodes" used by medical personnel have a conductive "stud" connector that plugs into a "socket" at the end of a "lead" connecting the electrode to the ECG monitor, usually a bedside monitor but also in most Holter monitors. (2) "Dry electrodes" comprise of a conductive body contact without adhesive, liquid or gel, most often made of Ag/AgCl, stainless steel, conductive fabric or conductive silicone, while mechanical attachment to the skin is provided with a separate means such as a belt or a shirt. (3) a "patch" comprising a larger skin-compliant sticker with more than a single electrode embedded within that can be either of the "dry" or "wet" types. or (4) contactless electrodes that are capacitively coupled to a subject's body but have no direct electrical connection to the subject's skin. Additional types of electrodes exist.

Some sensors that may be used in WPM require direct skin contact (DSC) but not an electrical connection. DSC sensors may require, for example, mechanical, optical, audio or thermal coupling between said DSC sensor and the subject's body. These include but are not limited to respiration sensors such as piezoelectric "piezo" or piezoresistive pressure or force sensors, strain gauges, SeismoCardiograph (SCG) sensors including accelerometers, Stethoscope, PhotoPlethismogram (PPG) and/or Pulse Oximetry (SpO2/SaO2) optical sensors, optical/capacitive/other touch sensors, contact thermometers and IR thermometer optical windows.

A third group of non-skin contact (NSC) sensors require attachment to the subject's body but do not necessarily require skin contact. NSC sensors may require for example, mechanical, optical, audio or thermal coupling between said NSC sensor and the housing of a WPM and/or the environment surrounding the WPM. These include, for example, Inertial Measurement Units (IMU), ambient temperature sensors, ambient microphones, non-contact IR thermometers, proximity sensors, switches and user interfaces.

Advanced WPMs simultaneously measure several sensors of different types in order to provide data for sensor fusion algorithms, for analysis of patient conditions that show up in more than a single parameter and as backup to one another, for example, respiration rate can be detected from BioZ, pressure, ECG and PPG.

WPMs are often used to monitor ambulatory patients and required to be mechanically compliant to the shapes and topologies of different bodies and skin types and throughout the movement range of the subject's body, throughout different activities and postures. Furthermore, the subject's body is non-planar so it becomes a challenge to maintain continuous contact with the subject for all EP and DSC sensors simultaneously. This is somewhat an issue with 3 skin contact points (both EP and DSC) that need to conform to a subject's body contour and thus require at least some degree of flexibility and stretchability but becomes much more challenging in WPMs with 4 or more skin contact points.

One challenge in designing WPM is the mechanical design of such that enables both EP and DSC sensors to simultaneously and continuously contact the skin without impeding one another's proper operation while remaining very comfortable and ergonomic to the subject.

Impeding on this is the requirement of spacing between EP electrodes. For certain EP parameters such as ECG or EMG, the closer EP electrodes are to one another, the smaller the signal amplitude, decreasing the signal-to-noise ratio of the measurement. This means that the best signal is measured with electrodes spaced widely apart (for example, greater than 20 cm) while ergonomically WPMs are preferably as small as possible (for example, less than 10 cm) causing a design tradeoff between signal quality and ergonomics. This tradeoff is often solved by extending one or more of the electrodes beyond the minimal size of the WPM by means of a patch, wire leads or by imparting flexibility into the body of a larger WPM.

One challenge in designing WPM, particularly with dry electrodes and ambulatory monitoring, is that rubbing movement of the electrodes against the subject's skin introduces electrical artifacts that severely degrade the performance of EP sensors. It is thus important to design WPMs such that electrode placement is compliant to many body types and seamlessly adaptable to the subject's body movements and the skin contact points of the electrodes are maintained throughout the range of skin movement preventing rubbing movement of the electrodes against the skin.

A second challenge that users of rechargeable WPMs may face is the need for periodic charging. Typically, rechargeable batteries for WPM are either removable for charging separately or they are internal to the WPM. In the case of internal batteries, often a charging cable plug is connected into a socket on the housing of the WPM which may be a delicate tedious task.

TECHNICAL FIELD

Products and systems for measuring physiological parameter information from a subject's body.

BRIEF SUMMARY OF THE INVENTION

The present invention involves a wearable physiological monitor (WPM) that is attached to the body of a subject, and is configured to collect physiological parameter information from the body. The structure of attachment is unique in that that there are multiple legs attached to a subject's body that maximize the flexibility of movement of the body while still maintaining contact between the subject's body and a central housing, a direct skin contacting (DSC) sensor, and additional sensors in the legs. In some embodiments, the legs are attached directly to the subject's body, whereas in other embodiments they are attached to electrodes that are themselves attached to the body. In some embodiments, there is an elbow of flexible material between the legs and the central housing, attached to both of them, that allows maximum flexibility of relative movement along multiple of the six degrees of freedom (X-axis, Y-axis, Z-axis, pitch, yaw, and roll). In some embodiments, movement of the flexible elbow is monitored and measured, and the measurements provide information on one more physiological parameters of the body.

Some embodiments include a system with the WPM and a specialized strap, in which the strap attaches to a subject's body in various ways. In some embodiments, the strap has a hole in it for placement of a DSC sensor that is located on the bottom of a central housing. In some embodiments, there are one or more sensors embedded within the strap, in addition to the DSC sensor located directly on the central housing, where such embedded sensors may provide information about physiological parameters of a subject's body, and/or the movement of the flexible elbow as the subject's body moves.

Some embodiments include a charging base for charging a WPM. This charging base provides benefits superior to other charging bases, in that it allows accurate placement of the WPM in the charging base without fine alignment efforts of human or mechanical operators. It may do this is a variety of ways. In some embodiments, the walls of the base are tapered from wider on the top toward narrower on the bottom, such that when the WPM is placed in the charging base, gravity will cause the WPM to slide into the correct position in the base. In some embodiments, a magnetic field guides the WPM into the accurate position on the base. In some embodiments, gravity from tapered walls and a magnetic field are used together to guide the WPM into the correct position in the charging base.

BRIEF DESCRIPTION OF THE DRAWINGS

The objects, features, and advantages of the present invention will be apparent from the following detailed description of the preferred embodiments of the invention with reference to the following drawings.

DETAILED DESCRIPTION

Figure 1:
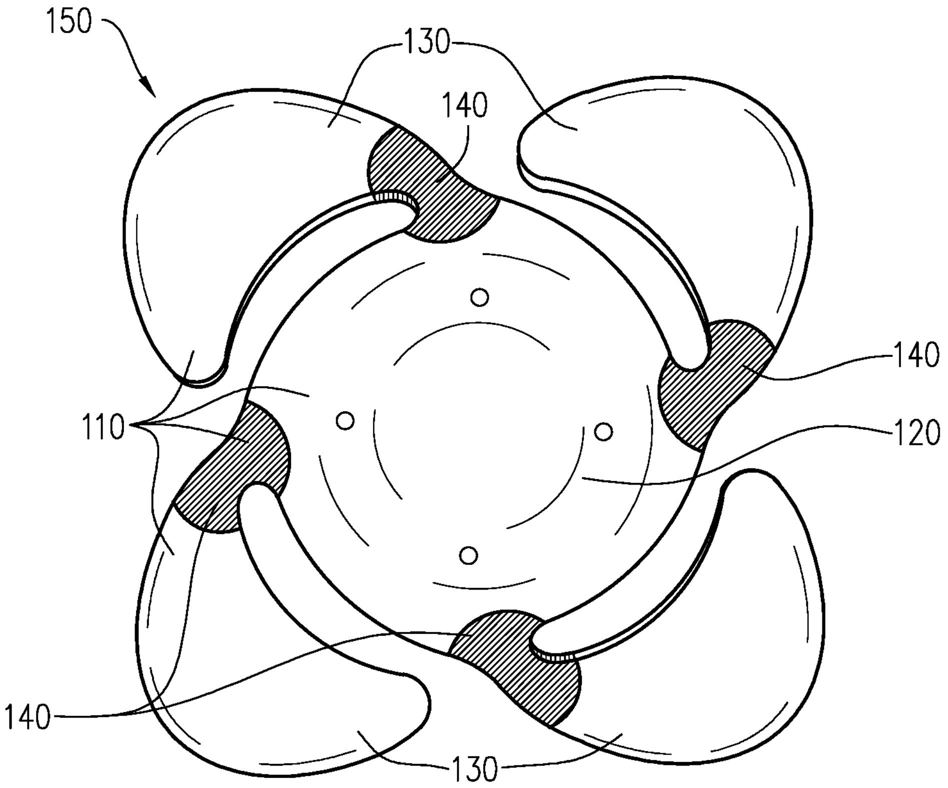
FIG. 1 illustrates a top view of a WPM including central housing, four rigid legs, and flexible elbows.

In this application, the following terms have the indicated meanings.

"Central housing": the main part of a WPM with the bottom in contact with a subject's body, the sides in contact with one more elbows, and including various mechanical or electrical components to receive and process information about the physiological parameters of the body.

"Charging base": a structure into which an WPM is placed in order to recharge a battery within the WPM.

"Communication function": one on the functions that may be executed by components within a central housing, in which information about physiological parameters is to communicated to a receiver placed distantly from a subject's body being monitored. Non-limiting examples of ways in which the function may be executed are Bluetooth, cellular, RFID, and WiFi.

"Computing function": one on the functions that may be executed by components within a central housing, in which information about physiological parameters is processed in some way for later storage or communication. Non-limiting examples of components that may be involved in the computing function a CPU, DSP, memory, and a micro-controller unit.

"Deformation": change in position along one or more of the six degrees of freedom. In some embodiments, the deformation of an elbow as the subject's body moves conveys information about a physiological parameter of that body.

"Degree of freedom": The three directions (X-axis, Y-axis, Z-axis) and the three types of rotation (pitch, roll, yaw) which together are considered the six ways of elasticity or flexibility, often known as the "six degrees of freedom."

"Direct skin contact (DSC)": a type of sensor that must be in direct contact with the skin of a subject's body in order to collect information about physiological parameters of the body. In some embodiments, there is a layer of material between a sensor and the skin, but the layer does not prevent the collection of information about physiological parameters of the body. For example, an optically transparent layer of material will not prevent the collection of optical information, or a thermally conductive layer will not prevent the collection of thermal information, or a mechanically compliant layer that moves with the skin will not prevent the collection of mechanical information. In all these examples, the sensor is not literally in direct contact with the skin, but it is in direct contact with a layer of material that does not disrupt the collection of information by the sensor, and in this way, the sensor is in virtual contact with the skin. A sensor in direct contact with such a layer of material still functions as a DSC sensor, and is included within that term.

"Elbow": the material that connects the central housing of a WPM to the legs.

"Electrode": an electrical conductor used to make contact with a nonmetallic part of a circuit. As used herein, hardware that interfaces electrical physiological parameters such as electrical potential and/or current from a subject's body to an Electro-Physiological (EP) sensor. Electrodes can also be used for auxiliary functions such as providing a DC voltage bias to the body.

Electrodes can be of several types (1) "wet electrodes" comprise of a conductive sponge or hydrogel embedded within an adhesive sticker that provides a mechanical connection to the skin, most off-the-shelf "ECG electrodes" used by medical personnel have a conductive "stud" connector that plugs into a "socket" at the end of a "lead" connecting the electrode to the ECG monitor, usually a bedside monitor but also in most Holter monitors. (2) "Dry electrodes" comprise of a conductive body contact without adhesive, liquid or gel, most often made of Ag/AgCl, stainless steel, conductive fabric or conductive silicone, while mechanical attachment to the skin is provided with a separate structure such as a belt or a shirt. (3) a "patch" comprising a larger skin-compliant sticker with more than a single electrode embedded within that can be either of the "dry" or "wet" types. or (4) contactless electrodes that are capacitively coupled to a subject's body but have no direct electrical connection to the subject's skin. Additional types of electrodes exist.

"Electro-physiological (EP) sensor": a type of sensor for collecting electrical signals from a subject's body using one or more electrodes. Different EP sensors can be used to collect a variety of physiological signals including, for example, but not limited to, ElectroCardiogram (ECG aka EKG), ElectroMyograph (EMG), Skin Conductance Level (SCL aka GSR), and Bio Impedance (BioZ).

"Interface or "user interface": a component that allows a person to create some kind of communication with a device. Non-limiting examples of such devices include button, buzzer, haptics, LCD, and LED.

"Leg": the structure of various embodiments that connects physically to the subject's body, either directly or through a pre-placed electrical socket. The leg also connects to the central housing, not directly but by attachment to an elbow that is itself connected to both the leg and the central housing. In some embodiments, a leg may include a "leg sensor". A leg may comprise rigid or flexible materials.

"Leg sensor": A sensor on a leg that may be one of three types. One leg sensor may measure a physiological parameter of a subject's body. A second leg sensor may measure the deformation of an elbow as the subject's body moves. A third leg sensor may collect information about the environment of the leg.

"Magnetic charging connector": a connector that creates an electrical connection for the purpose of charging a WPM, said connection mechanically assisted and/or aligned by attraction between magnets. For such charging, there must be at least one connector on the WPM and a complementary connector connected to a power source, for example, but not limited to, by a charging base or at the end of a charging cable.

"Non-skin contact (NSC)": a sensor that does not require contact with a subject's body. NSC sensors may collect physiological or non-physiological parameters. Some examples of NSC sensors include but are not limited to Inertial Measurement Unit (IMU), ambient temperature sensor, microphone, non-contact infrared thermometer and proximity sensors.

"Pitch": rotation about the Y-axis.

"Radial direction": a direction in the X-Y plane pointing outwards from a DSC sensor at the bottom of a central housing (or in the absence of such DSC sensor, then from the center of the bottom of the central housing).

"Roll": rotation about the X-axis.

"Sensor": a device for electrically detecting a physical parameter. Sensors may be of various types, including electrophysiological (EP) sensors that require electrical contact to a subject's body and to electrodes, DSC sensors that require non-electrical direct contact with the body, and NSC sensors that do not require skin contact. There may also be, in various embodiments, leg sensors that measure and monitor the deformation of an elbow as the subject's body moves—this is a type of NSC sensor. Sensors may detect physiological parameters for example, but not limited to, respiration or skin conductance, or non-physiological parameters, for example, but not limited to, ambient temperature or ambient sound.

"Socket": a type of fixed (non-mobile) connector that allows for electrical connection to an electrode. In the various embodiments herein, the term refers to female connectors only.

"Strap": In various embodiments, a structure that allows exerting a force on a central housing toward a subject's body. A strap may include physical aspects for a DSC sensor, and in some embodiments, for other kinds of sensors.

"Subject's body" or "body": The body of a living creature to which a WPM is attached directly or indirectly. The living creature may be a human, an animal, a bird, or any other living creature that is being monitored.

"Tangential direction": an arced line in the X-Y plane its center of rotation being on the DSC at the bottom of the central housing (or in the absence of such sensor, the center of the bottom of the central housing). The tangential direction is orthogonal to the radial direction.

"X-Y plane": the geometric plane that connects the sockets or the legs of various embodiments. If, for example, a device were laid "flat on a table", the X-Y plane is the plane of the table. Also, an X-axis orientation is the line passing through a DSC sensor at the bottom of the central housing (or lacking such sensor, the center of the bottom of the central housing) in the direction passing through the projection on the X-Y plane of a flexible elbow. Then the Y-axis is orthogonal to the X-axis in the X-Y plane passing through the projection on the X-Y plane of the flexible elbow, and the Z-axis is normal to the X-Y plane whereas the "down" direction of the Z-axis points towards the sockets and the table.

"Wearable physiological monitor (WPM)": a kind of hardware that is attached directly or indirectly to the subject's body, for the purpose of measuring or monitoring one or more physiological parameters of the subject's body. A WPM may include a sensor, various components to store or process data, and various components to communicate information to a remote transceiver.

"WPM strap" or just "strap": in various embodiments, a special strap that performs two or more functions. One function is to connect a WPM physically to a subject's body, pulling the central housing toward the body. A second function is to provide a place for an DSC sensor on the bottom of a central housing to make direct contact with a subject's body through a hole predesigned and manufactured in the strap. A third function, in some embodiments, is to contain additional sensors, which may be DSC sensors or EP sensors, to measure physiological parameters of a subject's body. A fourth function, in some embodiments, is to connect a WPM to a battery.

"Yaw": rotation about the Z-axis.

FIG. 1 illustrates a top view of a WPM including central housing, four rigid legs, and flexible elbows. Depicted is a top view of one embodiment of a WPM 110 including a central housing 120. In this example, four rigid legs 130 are connected to the central housing 120 via flexible elbows 140. The surface that the WPM is placed upon defines the X-Y plane 150 of the WPM 110.

Figure 2:
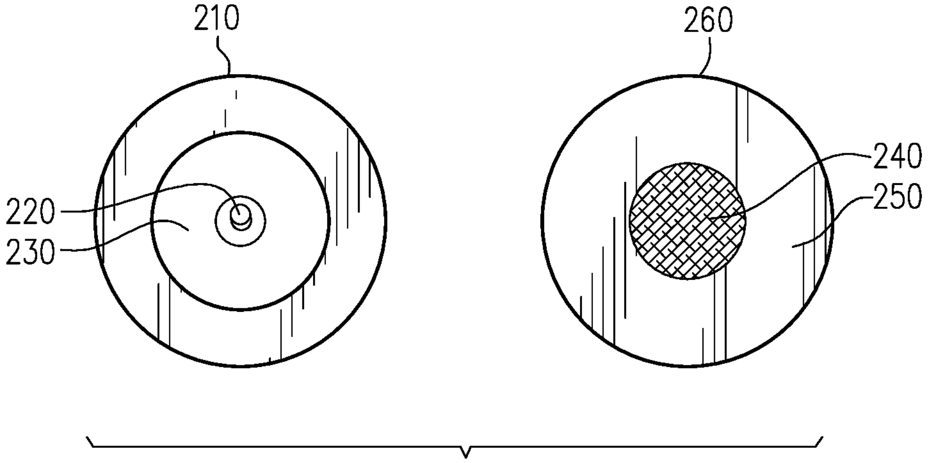
FIG. 2 illustrates a top view and a bottom view of a typical wet ECG electrode.

FIG. 2 illustrates a top view and a bottom view of a typical wet ECG electrode. Depicted are two views of a typical "wet" ECG electrode. There is a top view 210 at left and a bottom view 260 at right. This electrode exists in the prior art, in which bottom view 260 is directly connected to the subject's body. The top view 210 including a male "stud" electromechanical snap connector 220 which may attach to a socket on a WPM, surrounded by a flexible substrate 230. The bottom view 260 includes a conductive body contact 240 electrically connected to said stud and surrounded by skin adhesive 250 on the bottom of said flexible substrate 230 for connection to a subject's body.

Figure 3:
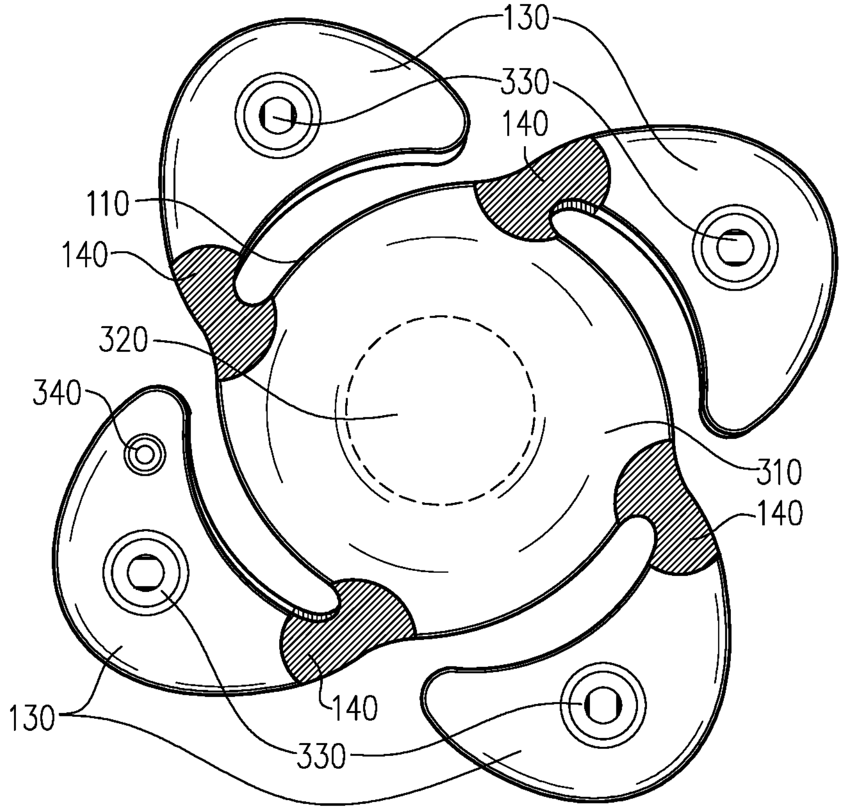
FIG. 3 illustrates a bottom view of a WPM with an embedded DSC sensor.

FIG. 3 illustrates a bottom view of a WPM with an embedded DSC sensor. Depicted is a bottom view of the WPM 110, including a bottom portion of the central housing 310, one or more DSC sensors embedded within 320, four legs 130 in this example, and four flexible elbows 140, where each leg is connected to the central housing 310 by its elbow. Each of the four legs 130 includes a female "socket" electromechanical snap connector 330. In addition, one of the legs may include an additional connector (a complementary connector 340), such as, as a non-limiting example, a magnetic charging connector. The embodiment depicted is illustrative only. There may be two, three, four, or more legs, though one or more legs will be connected to the central housing by an elbow. There may be more than one leg with a snap connector. There may be more than one leg with a magnetic charging connector. A charging connector may be non-magnetic. A charging connector may be assisted by magnets that are a separate component from the charging connector. A charging connector may be on the central housing. A leg may be connected to the central housing 310 by more than one elbow.

Figure 4:
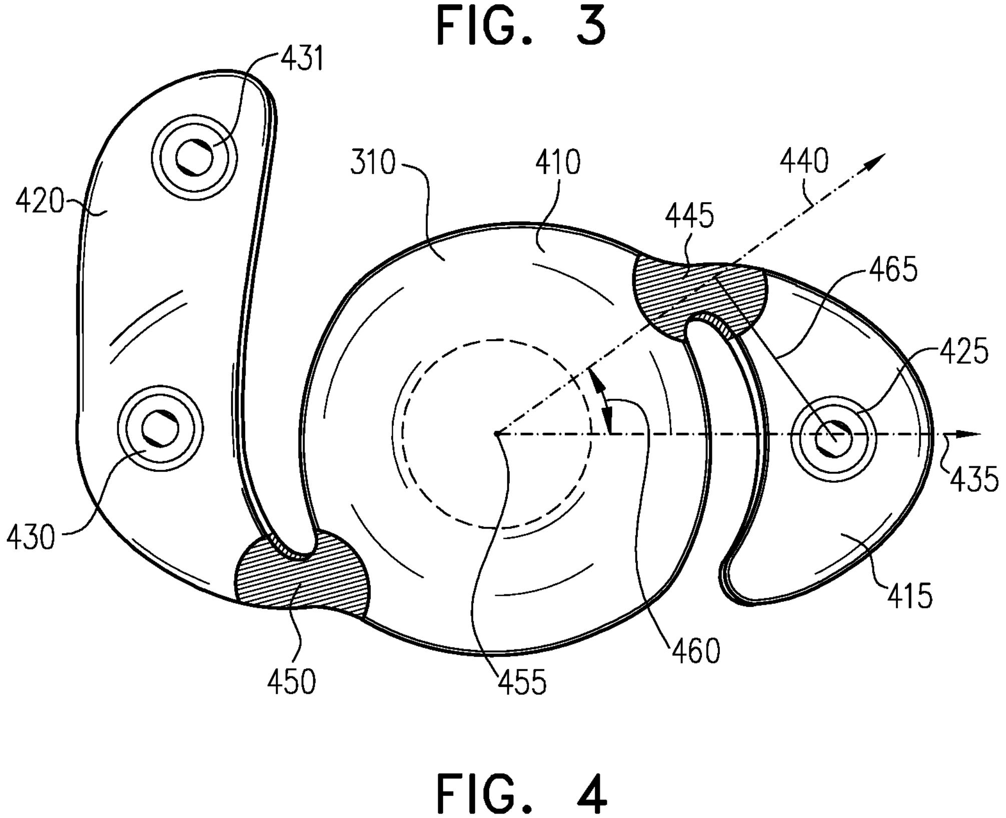
FIG. 4 illustrates a bottom view of a WPM with two legs and one socket, connected by elbows.

FIG. 4 illustrates a bottom view of a WPM with two legs each connected by an elbow, one of the legs having a single socket and the other leg having two sockets. Multiple sockets on one or more legs may support a required number of electrodes with fewer legs.

Depicted is a bottom view of a WPM 410 having two legs 415, 420. Leg 415 having one socket 425, and leg 420 having two sockets 430 and 431, both legs 415, 420 connected by an elbow 445, 450 with a central housing 310, comprising DSC sensor 455 on the bottom portion of the central housing 310.

A first reference line 435 is drawn from the DSC sensor 455 through socket 425 in a radial direction. A second reference line 440 is drawn from the DSC sensor 455 through elbow 445 that defines the X-axis for that leg 415 and elbow 445. In this exemplary embodiment, a non-insignificant angle 460 is formed between said first reference line 435 and second reference line 440. Also, in this exemplary embodiment, a mechanical lever 465 is formed between the socket 425 and the bending axis defined by the second reference line 440 through the elbow. The mechanical lever 465 converts translational movement of the socket 425 in the X/Y/Z directions to rotational deformation of the elbow 445 in the pitch/roll/yaw directions. Elbow 445 also deforms due to pitch/roll/yaw of the socket 425 and the leg 415.

Applying the mechanical lever principal thus gives the leg and the attached electrode multiple degrees of freedom without resorting to highly elastic materials, serpentine geometry, axes or rails. The mechanical lever 465 also transfers mechanical attachment force from the legs through the elbow 445 to the central housing 310 (unlike a simple cable or wire connection found in prior art), assisting to keep a WPM 110 having a DSC sensor reliably in contact with the skin throughout the range of body movement and postures.

To assist these functions, the elbow 445 part itself may be of limited elasticity ("stretchiness") when pulled along the X-axis in comparison with alternative geometries, for example, but not limited to, extending in length under a pull of 10 Newtons by less than 5 mm, or alternatively, but not limited to, by less than 2 mm, or alternatively by less than 1 mm, or by any other relation of force to stretching.

Figure 5:
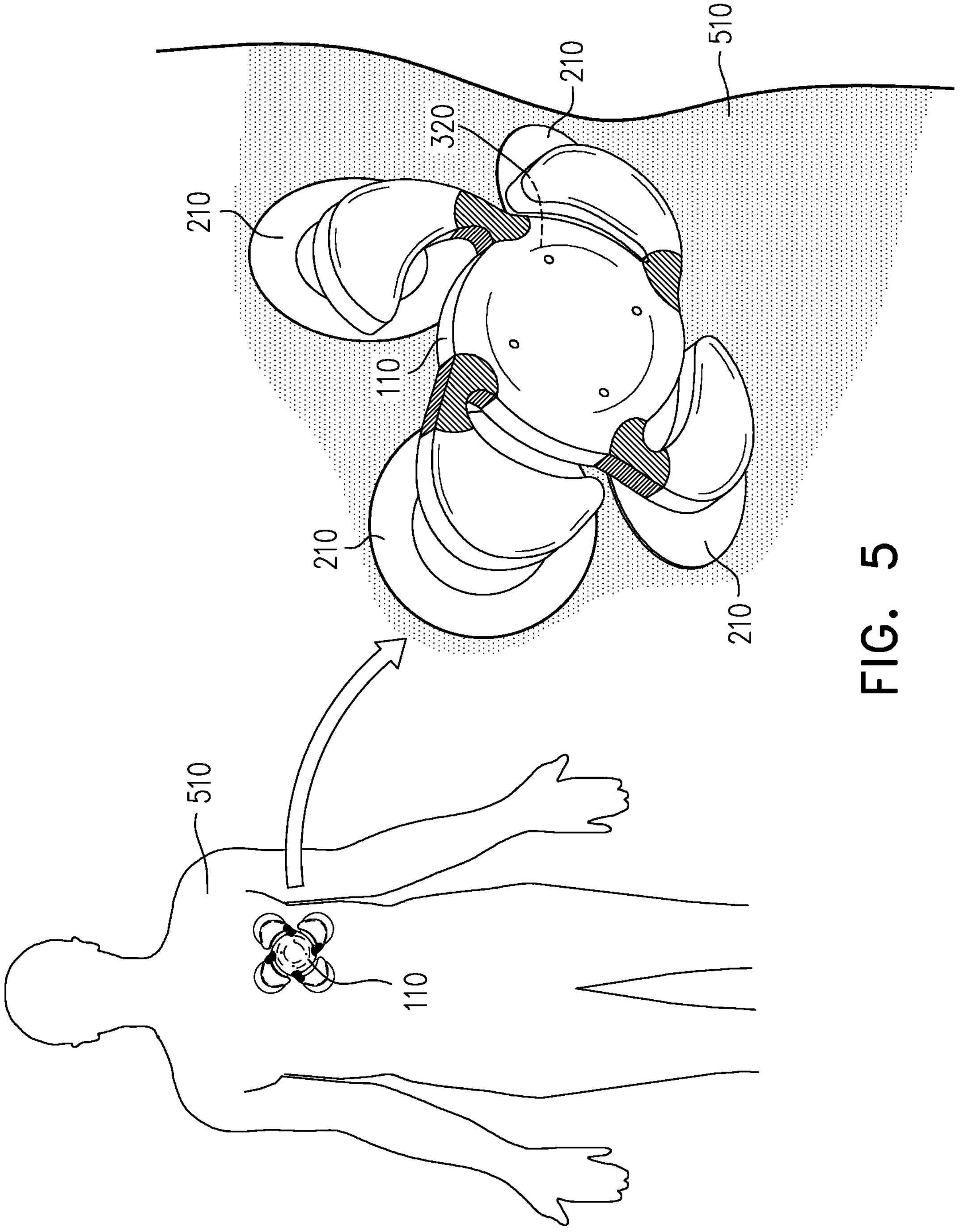
FIG. 5 illustrates a top view of a WPM in which an electrode on each of four legs is applied to a subject's body.

FIG. 5 illustrates a top view of a WPM in which an electrode on each of four legs is applied to a subject's body. Depicted is a WPM 110, similar to those shown in FIGS. 1 and 3, to which four electrodes similar to those in FIG. 2 are attached to a subject's body 510—that is well known in the art. However, as per various embodiments, each such electrode is connected to a central housing via a leg—that is, each electrode of FIG. 2 is connected to a leg via a socket (not shown here), and that leg is connected to the central housing by an elbow. In this way, the electrodes, however many there are in any embodiment, may be connected simultaneously to the central housing via a leg and an elbow. Further, the WPM may have a DSC sensor 320, which is located on the underside of the WPM and hence not shown here. Both the electrodes and the DSC sensor may be in simultaneous contact with the subject's body 510 (subject's skin) despite the particular contours of this body, and also despite the way the contour changes as the body moves.

Figure 6:
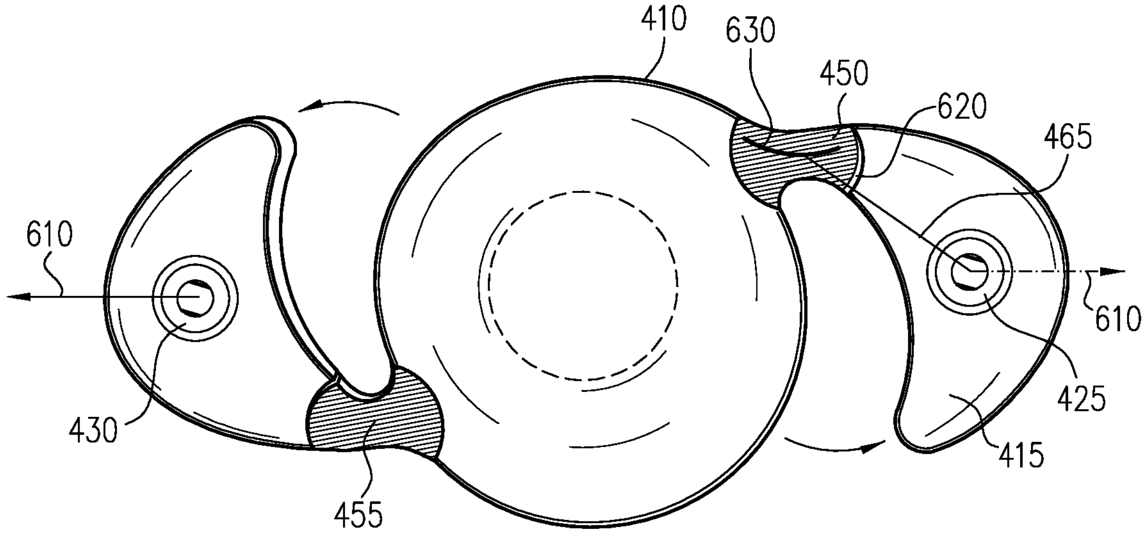
FIG. 6 illustrates a bottom view of a WPM with sockets pulled radially, causing flexing of at least one flexible elbow.

FIG. 6 illustrates a bottom view of a WPM with sockets puled radially, causing flexing of at least one flexible elbow. Depicted is a WPM 410 similar to that shown in FIG. 4 but with a single socket for each of two legs, wherein sockets 425, 430 are pulled radially 610 causing flexing 620 of at least one the elbows 450, 455 due to action of the mechanical lever 465. The bend sensor 630 embedded within the elbow 450 is bent by the flexing of the elbow, generating an electrical signal in response to said flexing, indicative of the puling force applied by the radial pull 610. Such signal could indicate a stretching of the skin between electrodes connected to sockets 425 and 430 by a variety of reasons, for example, as a result of the subject's breathing or posture. The degree and pattern of pulling may be used to monitor various physiological parameters.

Figure 7:
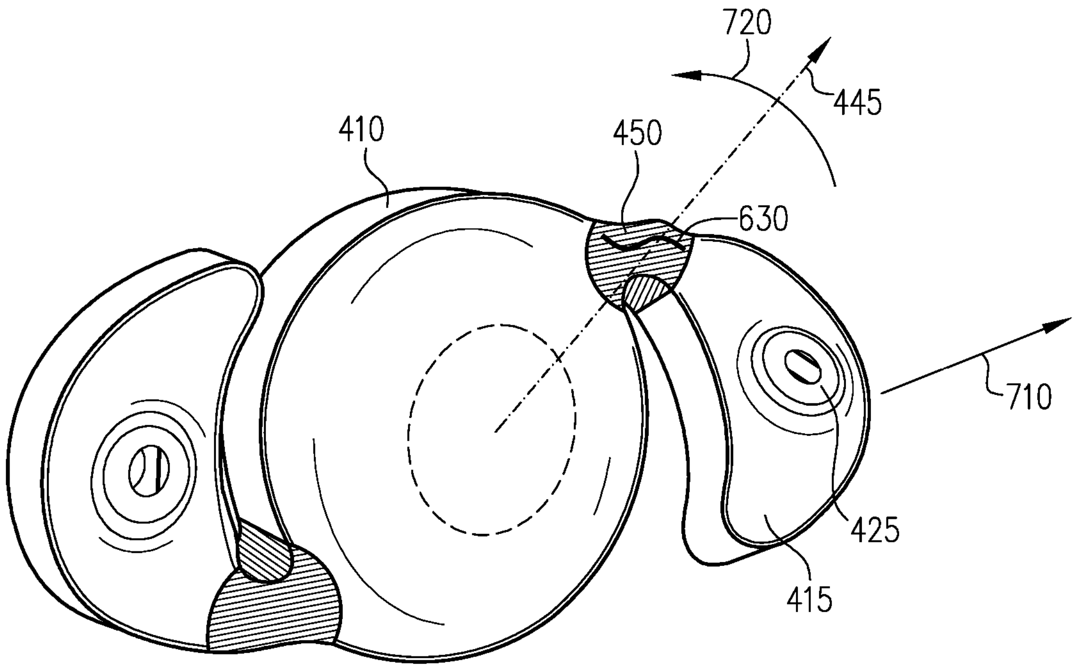
FIG. 7 illustrates a bottom view of a WPM with one socket displaced along the Z-axis causing a twist of the elbow and roll of a leg about the X-axis.

FIG. 7 illustrates a bottom view of a WPM with one leg displaced along the Z-axis causing a twist of the elbow and roll of a leg about the X-axis. Depicted is a WPM 410 similar to that shown in FIGS. 4 and 6, wherein one socket 425 is displaced in the Z-axis direction 710 causing a twist 720 of the elbow 450 and roll of the whole leg 415 about the X-axis 445. A bend sensor 630 is also embedded within elbow 450, and will twist coincident with the elbow, where the movement generates an electric signal in response to the displacement along the Z-axis direction 710. FIG. 7 depicts multiple degrees of freedom in movement while maintaining contact between sensors and the body either in the central housing or connected to the leg. Part of the information obtained is through the changing deformation of the elbow.

Figure 8:
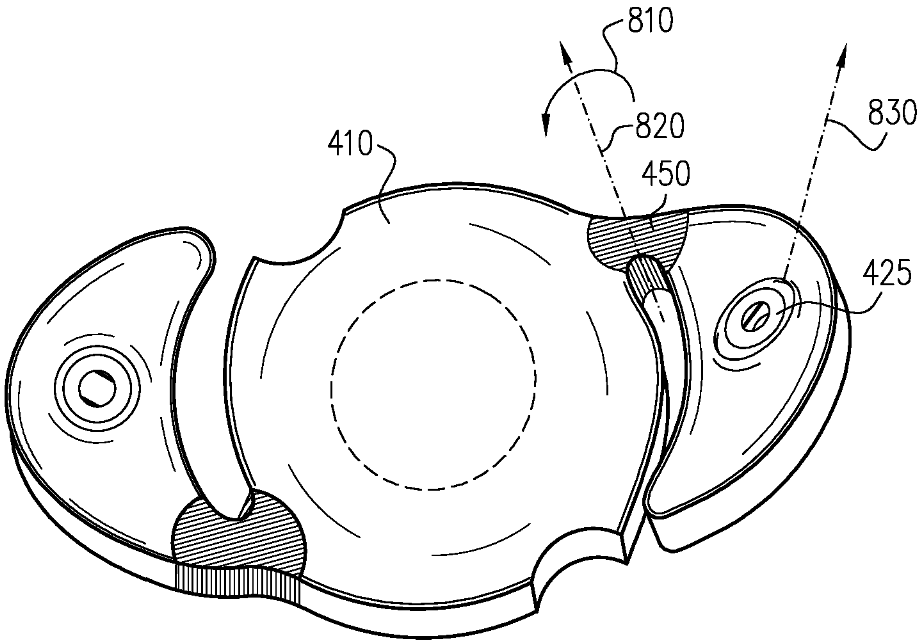
FIG. 8 illustrates a bottom view of a WPM with one socket having pitch about the Y-axis causing pitch in the elbow and Z-axis displacement of the socket.

FIG. 8 illustrates a bottom view of a WPM having one socket with pitch about the Y-axis causing a pitch in the elbow, and also Z-axis displacement of the socket. FIG. Depicted is a WPM 410 similar to that shown in FIGS. 4, 6 and 7, wherein one socket 425 has pitch 810 applied about the Y-axis direction 820 causing a pitch in the elbow 450 coupled with Z-axis displacement 830 of the socket.

Figure 9:
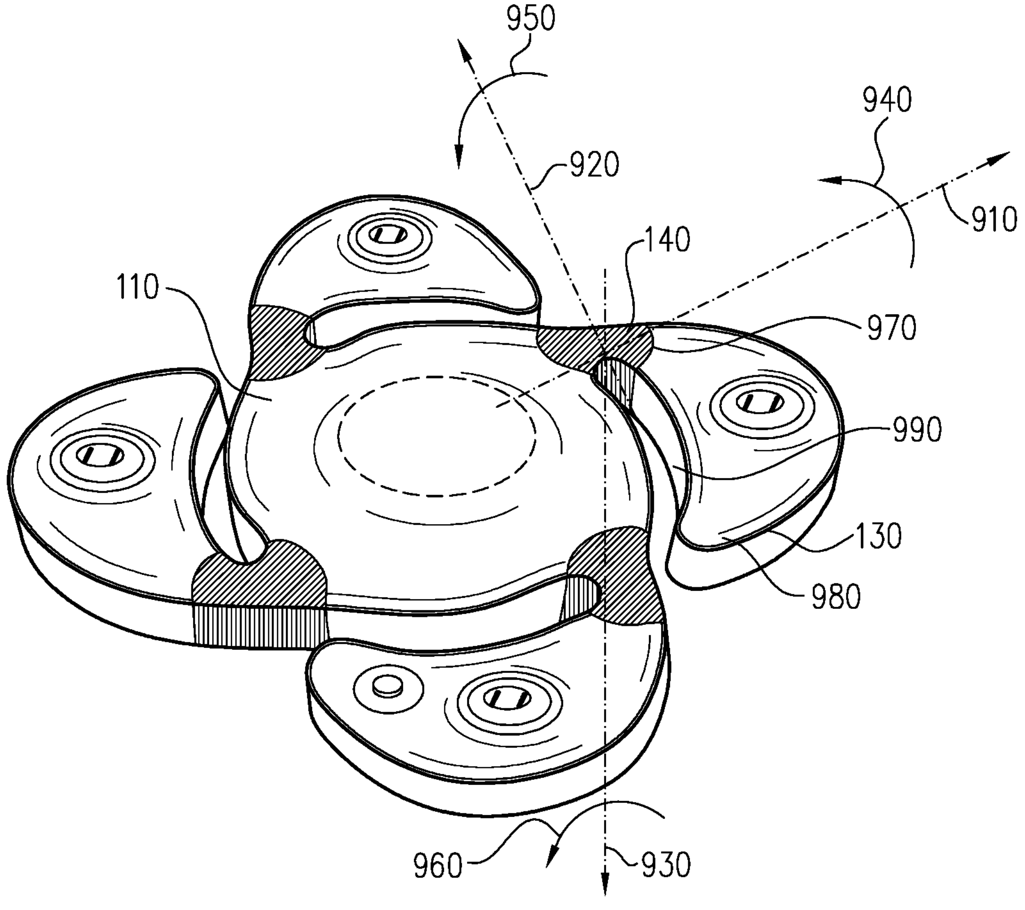
FIG. 9 illustrates a bottom view of a WPM with the six degrees of freedom illustrated for one elbow.

FIG. 9 illustrates a bottom view of a WPM with the six degrees of freedom illustrated for one elbow. Depicted is the bottom of a WPM 110 similar to that shown in FIG. 3 referring to elbow of the flexible elbows 140 for which the X-axis 910, Y-axis 920, Z-axis 930, roll 940, pitch 950 and yaw 960 directions are indicated. Also shown are the clockwise (as viewed from above) tangential end 970 (to which the elbow is attached in this embodiment), counter-clockwise tangential end 980, and a proximal edge 990 of a leg of the four legs 130.

Figure 10A:
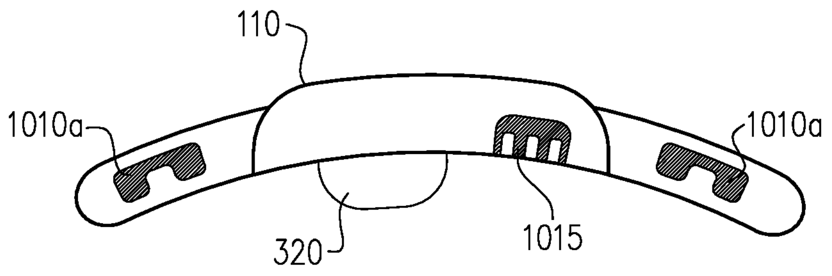
FIG. 10*a* illustrates a side cutaway of a WPM with a DSC sensor two EP socket connectors, and an auxiliary electrical socket.

FIG. 10*a* illustrates a side cutaway of a WPM with a DSC sensor two EP socket connectors, and an auxiliary electrical socket. Depicted is a side cutaway of a WPM 110 with central DSC sensor 320, two EP electrode electromechanical socket connectors 1010*a*, and an auxiliary electrical connector 1015.

Figure 10B:
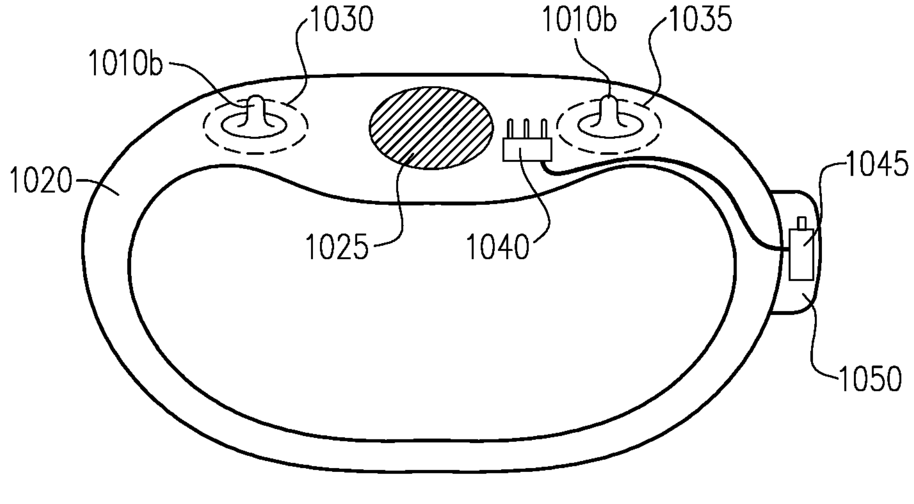
FIG. 10*b* illustrates a strap with a hole for a DSC sensor, connected to a subject's body, having stud connectors and EP electrodes.

FIG. 10*b* illustrates a strap with a hole for a DSC sensor, connected to a subject's body through stud connectors and EP electrodes. Depicted is a strap 1020 having a hole 1025 in a portion of the strap, two electromechanical stud connectors 1010*b* on the exterior side of the strap, each connected to an EP electrode on the interior side of the strap 1030, 1035 which may or may not be a dry electrode, and a connector 1040 wired to a battery 1045 within a pocket 1050. Said hole 1025 is such that a DSC sensor 320 may come in contact with a subject's body through said hole.

Figure 10C:
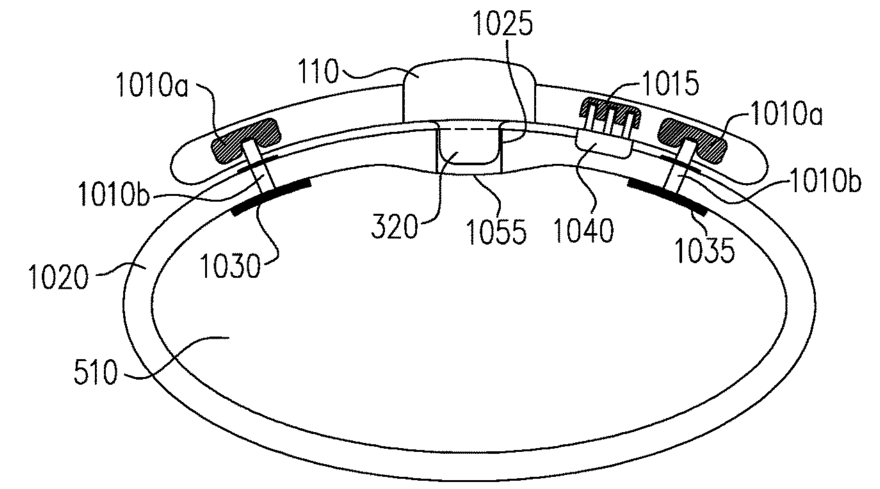
FIG. 10*c* illustrates the side cutaway of a WPM as shown in FIG. 10A, but now connected physically to the DSC sensor and subject's body as shown in FIG. 10B.

FIG. 10*c* illustrates the side cutaway of a WPM as illustrated in FIG. 10*a*, but now connected physically to the DSC sensor and subject's body as illustrated in FIG. 10*b*. Depicted is a cutaway view of the WPM 110 in FIG. 10*a* as attached to the strap 1020 illustrated in FIG. 10*b* while wrapped around a subject's body 510. Electromechanical socket connectors 1010*a* mate with electromechanical stud connectors 1010*b* connecting the WPM 110 to the strap 1020 both electrically and mechanically. Electrical connector 1015 mates with connector 1040 said connectors depicted without attachments for clarity but may connect the WPM to a battery and/or sensors within the strap. DSC sensor 320 presses against the subject's body 510 through hole 1025. This drawing also depicts an optional thin layer 1055 that is part of the strap, covering the hole between the DSC and the subject's body but functionally not interfering with operation of the DSC sensor.

Figure 10D:
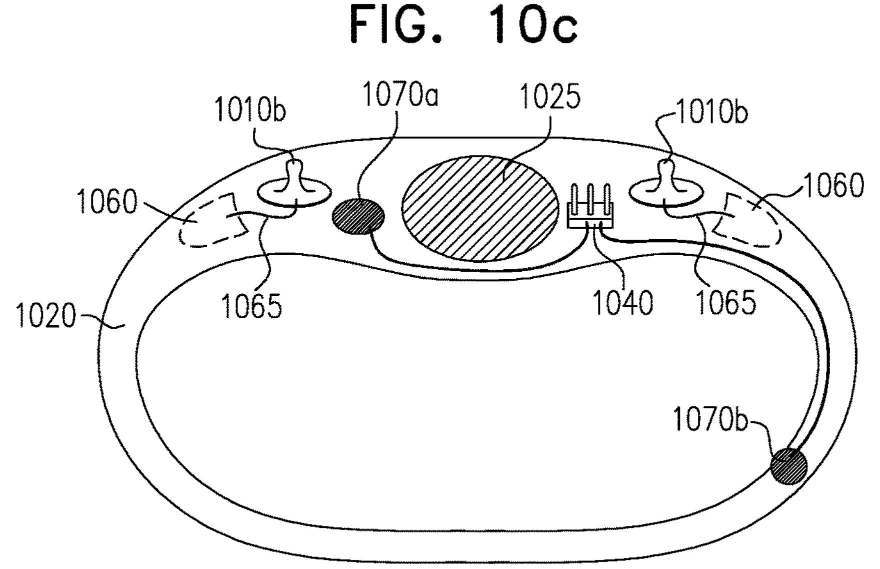
FIG. 10*d* illustrates another embodiment of a strap, in which EP electrodes are not directly connected to studs, but rather connected through some kind of conductor.

FIG. 10*d* illustrates another embodiment of a strap, in which EP electrodes are not directly connected to studs, but rather connected through some kind of conductor. Depicted is another embodiment of strap 1020 wherein skin contacting EP electrodes 1060, such as but not limited to dry electrodes or wet electrodes or contactless electrodes, are not directly attached to electromechanical studs 1010*b* but rather connected via conductors 1065, which may be a metal wire, conductive fabric, conductive ink, metal foil, or any other conducting material. Additionally, in the embodiment illustrated, external sensors 1070*a* & 1070*b* are embedded within strap 1020 and are electrically connected to connector 1040.

Figure 10E:
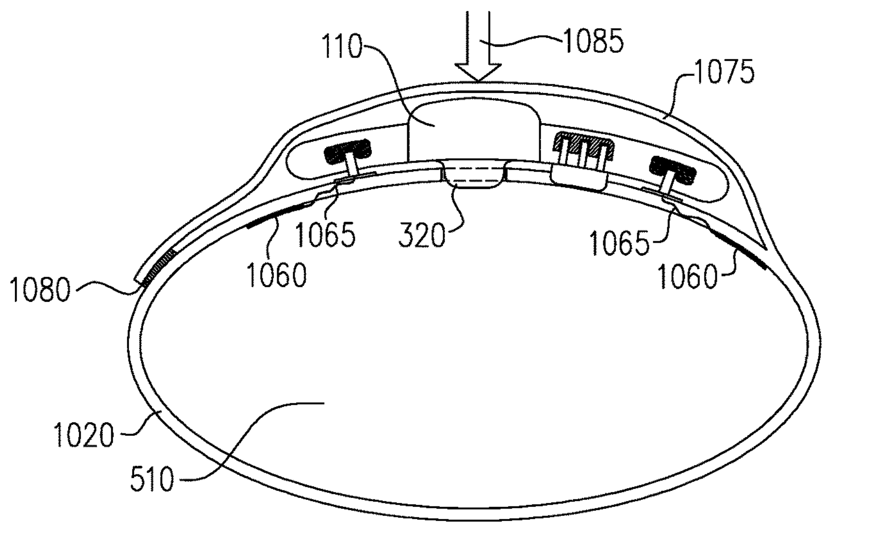
FIG. 10*e* illustrates a strap with a pocket or cover over the central housing of a WPM, where the pocket or cover is applying force on the central housing toward a subject's body.

FIG. 10*e* illustrates a strap with a pocket or cover over the central housing of a WPM, where the pocket or cover is applying force on the central housing toward a subject's body. Depicted is a strap 1020 having a pocket or cover 1075 over WPM 110 which may or may not be openable and/or adjustable by a fastener 1080 such as hook-and-loop fastener, magnet, snap or any other fastener, wherein the pocket or cover 1075 may apply a force 1085 on the WPM towards a subject's body 510 of the subject. Cover 1075 may protect the WPM 110 from accidental removal and from contamination while the force 1085 provided by it may improve the performance of the DSC sensor 320.

Figure 11:
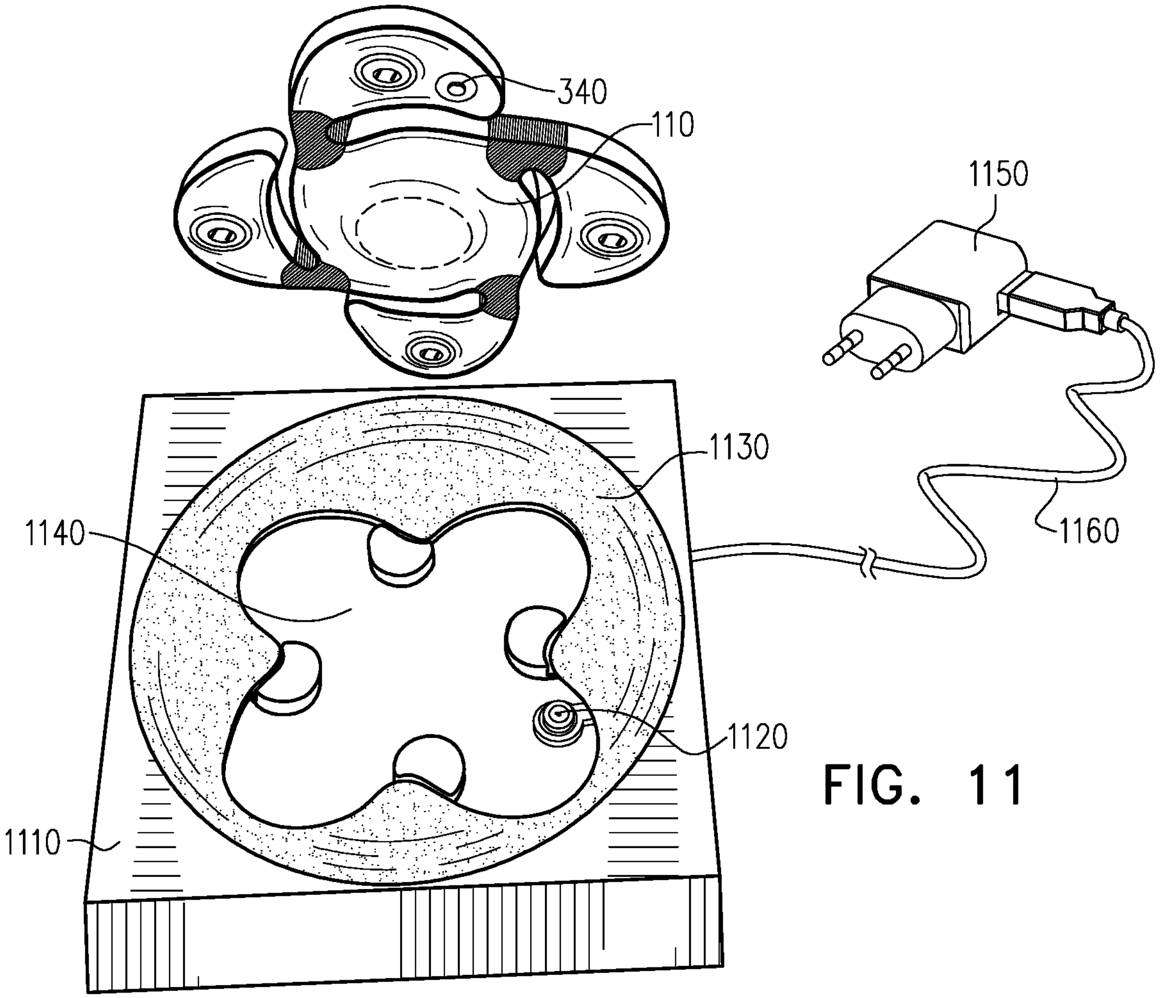
FIG. 11 illustrates a WPM and a charging base before the WPM is placed in the base.

FIG. 11 illustrates a WPM and a charging base before the WPM is placed in the base. Depicted are a WPM 110 and a charging base 1110 including a magnetic charging connector 1120 that can mate with a complementary connector 340 on the WPM. The charging base may have tapered walls 1130 to assist in alignment of the WPM to the charging position in addition to magnetic attraction and/or when no magnets are used. The charging base may have a central opening 1140 to assist in cleaning and prevent debris accumulation. The charging base may be powered by a power supply 1150 connected thereto via electrical cable 1160.

Figure 12A:
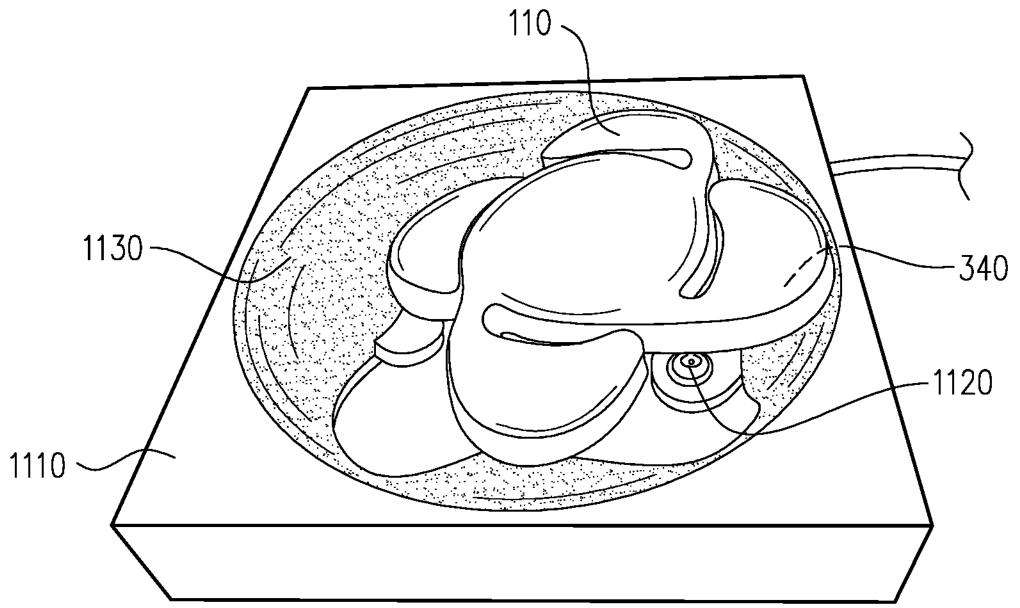
FIG. 12*a* illustrates a WPM placed in a charging base in an uncentered position.
Figure 12B:
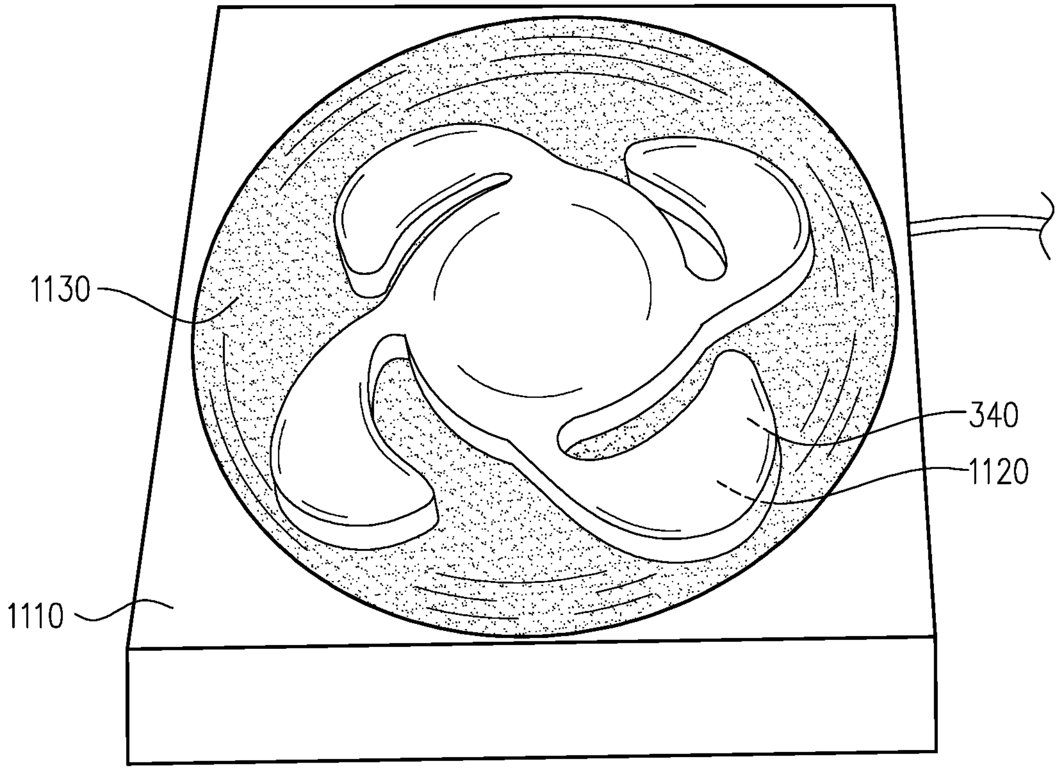
FIG. 12*b* illustrates a WPM placed in a charging base in a proper charging position.

FIG. 12*a* illustrates a WPM placed in a charging base in an uncentered position, whereas FIG. 12*b* illustrates a WPM placed in a charging base in a proper charging position. Depicted in FIG. 12*a* is a WPM 110 dropped into charging base 1110 from a certain elevation, landing at an orientation that is simultaneously uncentered, and at the incorrect pitch and/or incorrect yaw. The WPM 110 is then reoriented to the proper charging position as depicted in FIG. 12*b*. Due to the tapered walls 1130 of the charging base combined with the force of gravity, the WPM 110 is pushed towards the center of the charging base 1110. Due to the internal shape of the charging base, the WPM 110 is also rotated about the yaw axis to the correct orientation for charging shown in FIG. 12*b*. When in the correct orientation for charging, the proximity between the magnetic charging connector (1120, hidden from view in FIG. 12*b*) and the complementary connector (340, hidden from view in both FIGS. 12*a* and 12*b*) on the underside of the WPM 110 cause them to attract and connect to one another, thereby supplying power to the WPM 110 for recharging. In another embodiment the power is supplied via inductive charging coils rather than magnetic-electric sockets mating. In yet another embodiment the electrical contact is produced by spring loaded "pogo pins" for example in the charging base, mating with electrical contacts for example on the WPM housing exterior (or vice versa) while being held in contact by gravity alone or by gravity assisted by magnetic attraction between a magnet in the charging base and a magnet in the WPM or by mechanical force pressing the WPM towards the charging base. The structures described herein, and their methods of use, do not require neither fine manual alignment of the WPM 110 to the charging base 1110, nor the use of force to connect the WPM 110 and the charging base 1110.

One embodiment is a wearable physiological monitor (WPM) configured to attach to a subject's body, comprising a central housing and a plurality of legs, wherein the central housing comprises a direct skin contacting (DSC) sensor for receiving physiological signals generated by a subject's body, a data processor for converting the signals into usable information, and a component for wirelessly communicating the information to a receiver. The DSC sensor is part of the bottom of the central housing, is in direct contact with the body, and is configured to wirelessly send physiological parameter information from the body to a receiver. Each of two or more legs of the plurality of legs [after reading the description, I realize that "leg" is used to describe what I previously referred to as "peripheral housing" and this term is redundant and not referenced in the text] attaches to the subject's body, and a flexible elbow connects between the leg and the central housing. The flexible elbow allows movement of the leg in respect to the central housing in three or more degrees of freedom. The leg and the DSC sensor are in contact with the subject's body throughout the body's range of motion. The narrowest part of the flexible elbow is less than half the width of the widest part of the leg. The length of the flexible elbow is less than the width of the widest part of the leg. This embodiment may be called "an initial case."

In the initial case WPM just described, at least one of the plurality of legs comprises a sensor configured to measure the deformation of the flexible elbow as the subject's body moves, wherein the deformation is the relative movement between the central housing and a leg, and such relative movement is related to a physiological parameter of the subject's body.

In the WPM just described, at least one of the monitored physiological parameters of the subject's body is selected from the group consisting of respiration, physical activity, and physical posture.

In the initial case WPM described above, the plurality of legs may be connected to the central housing in positions such that the legs hold the central housing in contact with the subject's body.

In the initial case WPM described above, the central housing may further comprise one or more electro-physiological electrodes.

In the initial case WPM described above, a leg may further comprise a Light Emitting Diode (LED) indicator.

In the initial case WPM described above, the WPM may further comprise a connector to a power source.

In the initial case WPM described above, the WPM may further comprise a wireless power receiver.

In the initial case WPM described above, the one or more legs may further comprise one or more electro-physiological electrodes for receiving one or more electro-physiological parameters from a subject's body.

In the initial case WPM described above, one or more of the legs may further comprise one or more DSC sensors selected from the group consisting of respiration sensors such as piezoelectric "piezo" or piezoresistive pressure or force sensors, strain gauges, SeismoCardiograph (SCG) sensors including accelerometers, Stethoscope, PhotoPlethismogram (PPG) and/or Pulse Oximetry (SpO2/SaO2) optical sensors, optical/capacitive/other touch sensors, contact thermometers and IR thermometer optical windows.

In the initial case WPM described above, the plurality of legs may further comprise one or more NSC sensors, such as, for example, but not limited to, Inertial Measurement Unit (IMU), temperature sensor, microphone, proximity, switches, and user interface.

In the initial case WPM described above, one or more legs may comprise one or more electro-physiological electrodes, at least one of such electrodes is releasably attached to one or more legs. Any release electrode may be added or taken away from the leg, or may be left on the leg but activated or deactivated at will.

One embodiment is a system for monitoring physiological signals from a subject's body, comprising a wearable physiological monitor (WPM) and a strap, wherein the WPM comprises a central housing for receiving physiological signals, a direct skin contact (DSC) sensor to receive signals directly from a subject's body, and connectors for connecting the WPM to the strap. The strap may be applied around a portion of a subject's body. The WPM is releasably attached to the strap. The subject's body is on a first side of the material of the strap and the WPM is on a second side of the material of the strap, and the strap comprises at least one hole through which said a DSC sensor may contact a subject's skin. This may be called "the initial strap system."

In the initial strap system, the connector may be a mechanical connector.

In the initial strap system, the connector may be an electrical connector.

In the initial strap system, the strap may be configured to apply pressure on the wearable physiological monitor such that the DSC sensor on the wearable physiological monitor is pressed towards a subject's body.

In the initial strap system, the strap may further comprise an EP electrode that attaches directly to a connector on the WPM through the material of the strap.

In the initial strap system, the strap may further comprise a battery that is in electrical connection with the WPM.

Various embodiments described herein present a novel charging base that allows an operator to quickly and easily connect a WPM having an internal battery to a charging power supply without the delicate manipulation of plugging into a socket. One embodiment is a charging base for charging a wearable physiological monitor (WPM), a power source, and a means to convey the power from the power source to the WPM. Any means that conveys power could suffice. Non-limiting examples include contacts, non-magnetic connectors, magnetic connectors, pogo pins, power transmission coil, power transmission antennas, or a combination thereof. The power conveying means may be wired or wireless. The conveying means conveys power specifically to a complementary receptor in the WPM. Non-limiting examples of a complementary receptor include contacts, non-magnetic connectors, magnetic connectors, pogo pins, power reception coils, power reception antennas (rectennas), or a combination thereof. The walls of the charging base are tapered such that the opening is significantly wider than the WPM at the top and narrower at the bottom. Thus, when the WPM is placed on the charger, the WPM will slide into the charging position by the force of gravity alone or by a combination of gravity and magnetic force.

In the charging base just described, the charging base may further comprise a locking mechanism that locks the WPM into the charging base mechanically or electrically or electromagnetically. The locking may be for the duration of the period of charging. Or the locking may be for a set period of time. Or the locking may be unlimited in time until mechanism unlocks either at the decision of a person or according to the happening of some condition in accordance with an algorithm. Or the unlocking may be possible only to an approved party. Or the locking may be controlled by a remote system. Or the unlocking may be controlled by a biometric identifier. Or the unlocking may be controlled by proximity of a device. Or the unlocking may require a key.

In one embodiment, the legs are rigid housings connected to the central housing by flexible elbow joints.

In one embodiment, an elbow may include flexible materials.

In one embodiment, an elbow may include one or more rigid axes.

In one embodiment, an elbow may include one or more elastic material parts.

In one embodiment, an elbow may include one or more springs.

In one embodiment, an elbow may be fully or partially made of silicone.

In one embodiment, an elbow may be fully or partially made of Polyurethane.

In one embodiment, an elbow may be fully or partially made of Thermoplastic polyurethane TPU.

In one embodiment, an elbow may be fully or partially made of Thermoplastic elastomer TPE.

In one embodiment, the legs are flexible and may or may not be continuous to the elbow joints or of the same material as the elbow joints. Even if the mechanical properties of the legs and elbow are not identical.

In one embodiment, the legs are semi-rigid with an internal rigid skeleton over-molded or otherwise surrounded in flexible material.

In one embodiment an elbow part is further subdivided into several sections which may or may not be of similar mechanical properties.

In one embodiment the elbow is not attached at a tangential end or edge of the leg but rather at some other point along the proximal edge of the leg such that the leg exceeds beyond the elbow in both tangential directions.

In one embodiment one elbow is attached to two or more legs such that said two or more legs share a single attachment to the central housing. For example, two legs may connect to a single elbow such that a T-shape is formed. Said two or more legs may be either rigidly or flexibly connected to one another with an elbow connecting them to the central housing.

In one embodiment a first leg is connected by an elbow to the central housing and a second leg is connected by an elbow to said first leg.

In one embodiment, there may be one or more channels passing through the elbow through which electrical connections may be made between the leg and the central housing. Said connections may pass analog signals and/or digital signals and/or control and/or power signals.

In one embodiment, the elbow is over-molded over one or more electrical connections between the leg and the central housing.

In one embodiment, electrical connections between the leg and the central housing are routed separately from the elbow.

In one embodiment there are 3 or more electrical conductors between a leg and the central housing.

In one embodiment there are 6 or more electrical conductors between a leg and the central housing.

In one embodiment there are one or more DSC sensors in one or more of the legs. A leg including DSC sensors may or may not also have a socket and/or other structure to attach an EP electrode to it.

In one embodiment a leg may comprise multiple sockets and/or other structure to attach multiple EP electrodes to it.

In one embodiment there is a sensor embedded within the flexible elbow portion that senses the force and/or deformation of said elbow. This sensor may be for example, but not limited to, piezoelectric, piezoresistive, strain gauge, load cell, inductive, mechanical, optical or magnetic.

In one embodiment there is mechanical coupling between deformation of the elbow to a sensor external to the elbow that senses the force and/or deformation of said elbow. This sensor may be for example, but not limited to, piezoelectric, piezoresistive, strain gauge, load cell, inductive, mechanical, optical, or magnetic. Examples of mechanical coupling in this context include, but are not limited to, a mechanical beam, cantilever, lever, linkage, pulley, shaft, or tendon.

In one embodiment, the flexing amplitude and direction of an elbow may be indicative of a physiological parameter such as but not limited to body movement, body posture, respiration, respiration volume, cardiovascular, digestive, or muscular effort.

In one embodiment, the relative position between a leg and the central housing is sensed by comparing two sensors, one in the leg and the other in the central housing. Some examples of this embodiment are, but not limited to, accelerometer or magnetometer sensors.

In one embodiment, the relative position between a first leg and a second leg is sensed by comparing two sensors, one in the first leg and the another in the second leg.

In one embodiment, the relative position between a leg and the central housing is sensed by a sensor in one of the parts and a sensed element in the other part. Some examples of this embodiment are, but not limited to, magnet-magnetometer, capacitive proximity, mutual inductance, self-inductance, electric field, acoustic/optical/radio time-of-flight, optical encoder, or optical triangulation.

In one embodiment, the relative position between a first leg and a second leg is sensed by a sensor in one of the legs and a sensed element in the other leg.

In one embodiment, the relative position between a leg and a central housing or a first and a second leg may be indicative of a physiological parameter such as but not limited to, body movement, body posture, respiration, respiration volume, cardiovascular, digestive, or muscular effort.

In one embodiment a leg includes one or more EP socket(s) and in addition includes support circuits connected to said socket(s). Non-limiting examples include over-current protection, over-voltage protection, ESD protection, EMI filtering, analog filtering, amplification, buffering, data conversion, signal processing or any other electronic circuits.

In one embodiment a leg may include devices, connectors or electronic circuits that are not sensors such as, but not limited to, a battery, communication, radio, debugging, a processor, a charging connector, power circuits, or user interfaces.

In one embodiment, a WPM may be attached to a "strap", which may also be a belt or clothing article, wrapped around the subject or around a body part of the subject, including an attachment for the WPM and including electrodes that attach to the strap or are part of the strap such as dry electrodes or wet electrodes or contactless electrodes, whereas said electrodes are electrically connected to said WPM. Said strap may include clastic materials for comfort and ergonomics and the WPM preferably does not impede these traits, for example by employing the mechanical design described herein.

In one embodiment, a strap is designed to apply force on the WPM to maintain skin contact with a DSC sensor in the WPM.

In one embodiment, said strap includes a pocket wherein the WPM is mounted.

In one embodiment, said strap includes a flap that may cover the external (upper) side of the WPM for example after attachment of the WPM to the strap.

In one embodiment, said strap has a way of adjusting its size.

In one embodiment, said strap has a way of adjusting its tightness when applied to a subject's body.

In one embodiment, said strap has a structure for opening and closing for example but not limited, to a buckle, hook-and-loop, magnets, or zipper.

In one embodiment, a strap includes a hole, cutout or other opening to enable the DSC of the WPM to come in direct contact with the subject's skin.

In one embodiment, a strap includes a layer of flexible material to enable one or more DSC sensors of the WPM to indirectly contact or couple to the subject's skin through said layer. For example, a DSC optical sensor may operate through an optically transparent layer, a DSC temperature sensor may operate through a thermally conductive layer, or a DSC pressure sensor may operate through a mechanically compliant layer. For clarity, in the context of this clause, the "DSC" does not in fact have direct skin contact however said layer enables the sensors to operate as intended despite said layer between the DSC sensor and the subject's body.

In one embodiment, a WPM directly attaches to electrodes or includes integrated electrodes, for example dry electrodes or wet electrodes, and a strap is applied over the WPM to apply force on the WPM towards the subject's body to maintain reliable skin contact of a DSC sensor in the WPM and/or to maintain electrical contact of said electrodes to the subject's body and/or to reduce rubbing of said electrodes across the subject's skin.

In one embodiment, a strap including an attachment for the WPM and including electrodes that attach to the strap or are part of the strap such as dry electrodes or wet electrodes, whereas said electrodes are electrically connected to said WPM, additionally includes a section that applies over the WPM to apply force on the WPM towards the subject's body. For example, the WPM may be attached within a pocket, or for example a detachable flap may cover the WPM when attached.

In one embodiment, a strap includes an attachment for the WPM and includes electrodes that attach to the strap or are part of the strap such as dry electrodes or wet electrodes or contactless electrodes, whereas said electrodes are electrically connected to said WPM directly both electrically and mechanically. For example, but not limited to, by socket-stud, or by a clamp, or via other electromechanical connector.

In one embodiment, a strap includes an attachment for the WPM and includes electrodes that attach to the strap or are part of the strap such as dry electrodes or wet electrodes or contactless electrodes, whereas said electrodes are electrically connected to said WPM by an electrical connector and are mechanically attached to the strap.

In one embodiment, a strap including an attachment for the WPM and including electrodes that attach to the strap or are part of the strap such as dry electrodes or wet electrodes or contactless electrodes, are mechanically attached to the strap and electrically connected to the WPM via conductive thread or conductive fabric.

In one embodiment, a strap including an attachment for the WPM further includes one or more embedded sensors therein that may be electrically connected to the WPM but are not part of the WPM. Non-limiting examples include additional EP electrodes, additional DSC sensors, or additional non-skin contact (NSC) sensors.

In one embodiment, a strap including an attachment for the WPM further includes a power source therein, for example, but not limited to, a battery, or a wireless power receiver, that is electrically connected to the WPM but is not part of the WPM. For example, this may extend battery life or may allow the WPM to be smaller and lighter.

In one embodiment, one or more legs include a magnetic charging connector, and the system additionally includes a charging base that mates with said magnetic charging connector to recharge the WPM.

In one embodiment, the central housing includes a magnetic charging connector, and the system additionally includes a charging base that mates with said magnetic charging connector to charge the WPM.

In one embodiment, the WPM charging connector may or may not be magnetic and attachment and alignment of the WPM to the charging base is aided by magnets in the WPM and/or the charging base and/or the charging connector such that the WPM can be dropped into the charging base and the charging contacts align and connect. In this context "dropped" means that there is a relatively large range of spatial locations from which releasing a handheld WPM above the charging base will cause the WPM to align with the charging base and create an electrical charging contact, for example, but not limited to, over 5 mm or 10 mm or 20 mm or 50 mm offset in the X, Y or Z directions and for example, but not limited to, over 5 degrees or 10 degrees or 30 degrees or 90 degrees in the pitch, roll or yaw directions.

In one embodiment, attachment and alignment of the WPM to the charging base is aided by gravity and geometry of the charging base such that the WPM can be dropped into the charging base and the charging contacts align and connect.

In one embodiment, magnets, gravity and geometry together aid in attachment and alignment of the WPM to the charging base.

In one embodiment, said geometry includes tapered walls in roughly the perimeter shape of the WPM such that the taper realigns the WPM to the proper charging location if the WPM was dropped with an X and/or Y offset into the charging base.

In one embodiment, wireless charging may be used, there is no charging connector, and magnets, gravity and/or geometry align the WPM into the wireless charging base such that the charging coils of the WPM and of the charging base are aligned for charging.

In on embodiment, the wireless charging is inductive and comprises a power transmission coil in the charging base and a power reception coil in the WPM.

In one embodiment, said charging base includes additional electrical connections to the WPM, for example a data transfer connection.

In one embodiment, said charging base can additionally be used as a storage box.

In one embodiment, said charging base can additionally be used as a shipping box.

In one embodiment, the charging base may be mechanically or electrically locked to prevent unauthorized removal of the WPM from the charging base.

In one embodiment, said charging base lacks a central portion such that it has an opening through it that may aid in cleaning and may prevent accumulation of liquids and debris at the bottom of the charging base. Said opening may be considerably larger than a draining hole, for example, but not limited to, over 10 $mm^2$ or 50 $mm^2$ or 200 $mm^2$.

In one embodiment, said charging base supports more than one orientation of the WPM.

In one embodiment, magnets in the charging base and in the WPM may intentionally or unintentionally repel one another, for example to discourage or prevent incorrect orientation of the WPM into the charging base.

In one embodiment, said charging base additionally includes a mechanical structure such as, but not limited to, a clip, friction, springs, magnets, or geometry, that firmly holds the WPM once inserted into the charging base and until intentionally overcome by an operator's action to remove the WPM from the charging base. This may prevent the WPM from accidental disconnection from the charging base due to mishandling the charging base and/or enables different charging base orientations.

In one embodiment a charging base may be placed either horizontally and/or vertically and/or attached to a vertical surface.

In one embodiment two or more charging bases may be stackable to create a multi-unit charging station.

In one embodiment two or more charging bases may attach mechanically to one another. For example, but not limited to, by screws, tabs, rails, magnets, socket-stud, or electromechanical connectors.

In one embodiment two or more charging bases may connect electrically to one another.

In one embodiment said mechanical attachment and said electrical connection are performed simultaneously, for example by an electromechanical connector or for example by electrical contacts that are closed whenever a mechanical attachment is made.

In one embodiment a first charging base may have a power input connector and a power output connector such that a second charging base power input may connect to the first charging base power output connector (in a "daisy chain") and draw power from the first charging base.

In one embodiment, an infrastructure frame connects to two or more charging bases mechanically and/or electrically to form a multi-unit charging station.

In one embodiment, said infrastructure frame may be connected to a power source and may or may not provide power to one or more charging bases connected thereto.

In one embodiment a charging base may additionally include one or more ways of communication for example, but not limited to, Bluetooth, WiFi, Cellular, Radio, LoRa, modem, or ethernet.

In one embodiment an infrastructure frame may additionally include one or more ways of communication for example, but not limited to, Bluetooth, WiFi, Cellular, Radio, LoRa, modem, or ethernet.

In one embodiment, a charging base and/or an infrastructure frame may include two or more communication modes and can additionally function as a "gateway" and/or "bridge" and/or "router" and/or "hotspot" by passing data between a first and a second communication whereas at least one of said communication modes is wireless.

One of many possible examples may be but not limited to, a charging base and/or an infrastructure frame communicating over Bluetooth with one or more WPMs and communicating over a cellular data link with one or more cloud servers, and passing data and commands bi-directionally between said WPMs and said cloud servers.

In some embodiments, a charging base and/or an infrastructure frame may include one or more radios and may or may not include a processor and may or may not modify data and may or may not have a role in managing a communication network.

In one embodiment, a charging base and/or an infrastructure frame may communicate its own status to a second entity via a communication method. For example, but not limited to, communicating a charging fault, charging status, or power state, to a cloud server.

The invention has been described with reference to specific exemplary embodiments. Various modifications and changes may be made to such embodiments without departing from the broad spirit and scope of the invention. Accordingly, the drawings and specification are to be regarded as illustrative only, rather than restrictive or limiting.

We claim:

1. A wearable physiological monitor (WPM) configured to attach to a subject's body, comprising a central housing and a plurality of legs, wherein the central housing comprises a direct skin contact (DSC) sensor configured to directly contact skin of the subject's body when the WPM is worn by a subject for receiving physiological signals generated by the subject's body, a data processor for converting the signals into usable information, and a component for wirelessly communicating the information to a receiver;

wherein the DSC sensor is part of a bottom of the central housing, the DSC sensor is configured to directly contact skin of the subject when the WPM is worn by the subject, and the DSC sensor is configured to wirelessly send physiological parameter information from the subject's body to the receiver;

wherein each of two or more legs of the plurality of legs is configured to attach to the subject's body, and each of the two or more legs is attached to a respective flexible elbow positioned between respective leg and the central housing;

wherein the respective flexible elbow allows movement of a corresponding one of the two or more legs with respect to the central housing in three or more degrees of freedom; and each of the two or more legs and the DSC sensor are configured to remain in contact with the subject's body throughout a body's range of motion;

wherein the narrowest part of the flexible elbow is less than half a width of the widest part of the leg; and wherein a length of the flexible elbow is less than the width of the widest part of the leg.

2. The wearable physiological monitor of claim 1, wherein at least one of the plurality of legs comprises a sensor configured to measure a relative movement between the central housing and one of the two or more legs, and wherein the relative movement is related to a physiological parameter of the subject's body.

3. The wearable physiological monitor of claim 2, wherein the relative movement is measured by the sensor of a deformation of the flexible elbow.

4. The wearable physiological monitor of claim 2, wherein the physiological parameter of the subject's body is selected from a group consisting of respiration, physical activity, and physical posture.

5. The wearable physiological monitor of claim 1, wherein the plurality of legs is connected to the central housing such that the plurality of legs are configured to hold the central housing in contact with the skin of the subject when the WPM is worn by the subject.

6. The wearable physiological monitor of claim 1, wherein the central housing further comprises one or more electro-physiological electrodes.

7. The wearable physiological monitor of claim 1, wherein a leg further comprises a Light Emitting Diode (LED) indicator.

8. The wearable physiological monitor of claim 1, wherein the wearable physiological monitor further comprises a connector to a power source.

9. The wearable physiological monitor of claim 1, wherein the wearable physiological monitor further comprises a wireless power receiver.

10. The wearable physiological monitor of claim 1, wherein one or more legs further comprise one or more electro-physiological electrodes for receiving one or more electro-physiological parameters from the subject's body.

11. The wearable physiological monitor of claim 1, wherein one or more legs further comprise one or more DSC sensors selected from a group consisting of respiration sensor, piezoelectric sensor, SeismoCardioGraph (SCG), accelerometer, PhotoPlethismogram (PPG), Pulse Oximetry sensor, and thermometer.

12. The wearable physiological monitor of claim 1, wherein the plurality of legs further comprise one or more NSC sensors selected from a group consisting of: Inertial Measurement Unit (IMU), temperature sensor, microphone, and user interface.

13. The wearable physiological monitor of claim 10, wherein an electrode of the one or more electro-physiological electrodes is releasably attached to one or more legs.

* * * * *